United States Patent [19]
Freeland

[11] Patent Number: 5,306,266
[45] Date of Patent: Apr. 26, 1994

[54] FLEXIBLE SPACERS FOR USE IN DISPOSABLE ABSORBENT ARTICLES

[75] Inventor: Mary E. Freeland, Loveland, Ohio

[73] Assignee: The Procter & Gamble Company, Cincinnati, Ohio

[21] Appl. No.: 994,023

[22] Filed: Dec. 21, 1992

[51] Int. Cl.⁵ .................. A61F 13/15; A61F 13/20
[52] U.S. Cl. ................. 604/385.1; 604/358; 604/369; 604/378
[58] Field of Search ......... 604/358, 369, 378, 385.1

[56] References Cited

U.S. PATENT DOCUMENTS

| | | |
|---|---|---|
| 2,043,325 | 6/1936 | Jackson, Jr. . |
| 3,815,601 | 6/1974 | Schaefer . |
| 3,994,298 | 11/1976 | Des Marais ............... 604/369 |
| 4,382,443 | 5/1983 | Shafer et al. . |
| 4,559,051 | 12/1985 | Hanson .................. 604/385.1 |
| 4,560,380 | 12/1985 | Tharel . |
| 4,662,877 | 5/1987 | Williams . |
| 4,681,577 | 7/1987 | Stern et al. . |
| 4,731,065 | 3/1988 | Yamada . |
| 4,834,737 | 5/1989 | Khan . |
| 4,891,847 | 1/1990 | Baker et al. . |
| 4,892,536 | 1/1990 | Des Marais . |
| 4,895,568 | 1/1990 | Enloe . |
| 4,988,344 | 1/1991 | Reising et al. ............ 604/378 |
| 4,990,147 | 2/1991 | Freeland . |
| 5,037,416 | 8/1991 | Allen et al. . |
| 5,062,840 | 11/1991 | Holt et al. . |
| 5,176,672 | 1/1993 | Bruemmer et al. .......... 604/378 |
| 5,207,663 | 5/1993 | McQueen ................ 604/385.1 |
| 7,811,206 | 12/1993 | Dreier et al. . |
| 7,898,047 | 6/1992 | Allen et al. . |

FOREIGN PATENT DOCUMENTS

| | | |
|---|---|---|
| 0340320 | 11/1989 | European Pat. Off. . |
| 0355740 | 2/1990 | European Pat. Off. . |
| 0433951 | 6/1991 | European Pat. Off. . |
| 0483730 | 5/1992 | European Pat. Off. . |
| 0486006 | 5/1992 | European Pat. Off. . |
| 2561078 | 9/1985 | France . |
| 2628761 | 9/1989 | France . |
| 2074875 | 11/1981 | United Kingdom . |

*Primary Examiner*—Randall L. Green
*Assistant Examiner*—P. Zuttarelli
*Attorney, Agent, or Firm*—Gerry S. Gressel; Larry L. Huston; Fredrick H. Braun

[57] ABSTRACT

A spacer for use in a disposable absorbent article is disclosed. The spacer has an outer cover and a plurality of discrete elements enclosed by the outer cover. The discrete elements can move relative to one another within the outer cover. Relative movement of the discrete elements permits the spacer to plastically deform in response to flexural loading, while maintaining a fecal void space in the absorbent article under compressive loading.

25 Claims, 4 Drawing Sheets

FLEXIBLE SPACERS FOR USE IN DISPOSABLE ABSORBENT ARTICLES

CROSS REFERENCE TO RELATED APPLICATIONS

This Patent Application cross-references and incorporates by reference the following Patent Applications assigned to The Procter & Gamble Company: U.S. patent application Ser. No. 07/811,206, Disposable Absorbent Article Having Core Spacers, filed Dec. 20, 1991, by Dreier et al.; and U.S. patent application Ser. No. 07/898,047, Spacers for Use in Disposable Absorbent Articles and Disposable Articles Having Such Spacers, filed Jun. 11, 1992 by Allen et al.

FIELD OF THE INVENTION

The present invention relates to a spacer for use in disposable absorbent articles, and more particularly, to spacers forming a void space in a disposable absorbent article for isolation of fecal material from the wearer. The present invention also relates to disposable absorbent articles having such spacers.

BACKGROUND OF THE INVENTION

Disposable absorbent articles are well known in the art. Disposable absorbent articles are used to absorb and retain urine and fecal material. A particularly desired feature of disposable absorbent articles is the capability to minimize the task of cleaning of fecal material which is present on the wearer's skin after the soiled disposable absorbent article is removed from the wearer. In order to achieve this end, and to minimize epidermal contact and the associated irritation caused by the fecal material, attempts have been made to confine the fecal material to limited portions of the disposable absorbent article.

References in the prior art disclose a cavity or cutout in the absorbent core to receive the fecal material. The fecal material passes through the topsheet and is received by the material removed from or otherwise displaced from the absorbent core (such as through compression). However, these references suffer from the drawback that a cavity in the absorbent core or a removal of material from the absorbent core decreases its absorbent capacity. The cavity is limited in volume by the size of the absorbent core. Examples of such teachings include U.S. Pat. No. 2,043,325 issued Jun. 9, 1936 to Jackson, Jr.; U.S. Pat. No. 4,731,065 issued Mar. 15, 1988 to Yamada; U.S. Pat. No. 4,834,737 issued May 30, 1989 to Khan; and U.S. Pat. No. 5,062,840 issued Nov. 5, 1991 to Holt et al.

One attempt to minimize the task of cleaning of fecal material from the skin of the wearer is to provide a void space in the disposable absorbent article to receive the fecal material and to isolate it from the skin of the wearer. Typically, the void space is intermediate the topsheet which contacts the skin of the wearer and the absorbent core which absorbs fluid excretions, such as urine. In this arrangement, the topsheet may have an aperture or other passageway which communicates the fecal material into the void space.

Many of these references also disclose various arrangements for providing elastic extensibility to the topsheet relative to the aperture therethrough and the absorbent core. Examples of such teachings include U.S. Pat. No. 4,662,877 issued May 5, 1987 to Williams; commonly assigned U.S. Pat. No. 4,892,536 issued Jan. 9, 1990 to DesMarais et al.; and commonly assigned U.S. Pat. No. 4,990,147 issued Feb. 5, 1991 to Freeland. However, these references suffer from the drawback that the void space for receiving fecal material typically does not remain open when the wearer is in a sitting position or after the first loading has occurred.

To overcome this problem, other references teach adding a spacer to the disposable absorbent article. The spacer may be transversely oriented, generally horseshoe shaped, or may comprise longitudinally oriented parallel or divergent members. Examples of such references include European Patent Application 0,355,740 A2 published Feb. 28, 1990 in the name of Enloe; UK Patent Application GB 2,074,875 A published Nov. 11, 1981 in the name of Edwards; French Patent Application 2,561,078 published Sep. 20, 1985 in the name of Lefebvre; U.S. Pat. No. 4,382,443 issued May 10, 1983 to Shafer et al.; and U.S. Pat. No. 4,560,380 issued Dec. 24, 1985 to Tharel.

Spacers generally have a planar undeformed configuration. The spacer thickness controls the maximum void space height that can be maintained in the absorbent article. A minimum thickness is necessary to maintain a void space sufficient to receive the fecal material. Spacers are flexurally loaded, or bent, about one or more axes as the spacers are forced to conform to the wearer's anatomy or to deform in response to the wearer's movements.

Known spacers suffer from the drawback that they exhibit flexural rigidity, or resistance to bending or torsion when flexurally loaded. Flexural rigidity reduces a spacer's ability to conform to curvature caused by the wearer's anatomy or to deform in response to the wearer's movements. Spacers which exhibit too much flexural rigidity are undesirable in that they can appear bulky in the absorbent article, and can cause discomfort to the wearer. However, flexural rigidity generally increases with thickness, so that increased spacer thickness results in a more bulky appearance and cause more discomfort to the wearer. Thus, conventional spacers undesirably provide increased void space height at the expense of increased spacer flexural rigidity.

Additionally, known spacers exhibit an elastic flexural resilience. When flexurally deformed, such as by bending, a known spacer will develop internal restoring forces that tend to restore the spacer to its original, or undeformed, shape. These restoring forces can be transmitted to the wearer through the structure of the disposable article, and cause the wearer discomfort or cause improper fit.

Accordingly, it is an object of this invention to provide a spacer which is capable of maintaining a minimum spacer thickness and minimum void space height under compressive loading. It is also an object of this invention to provide a spacer that exhibits relatively little flexural rigidity. It is a further object of this invention to provide a spacer that deforms plastically, rather than elastically, in response to flexural loading about any axis, so that the spacer does not develop restoring forces in response to flexural loading. Yet another object of this invention is to provide a spacer having a number of discrete elements enclosed in an outer cover, wherein each discrete element is capable of motion relative to the other discrete elements enclosed in the outer cover in response to flexural loading of the spacer.

SUMMARY OF THE INVENTION

The invention comprises a spacer for maintaining a fecal void space in a disposable absorbent article. Such a spacer can be incorporated into an absorbent article, such as a disposable diaper. The disposable diaper can have a liquid impervious backsheet, a liquid pervious topsheet attached to the backsheet to form a void space for receiving fecal matter intermediate the topsheet and the backsheet, and an absorbent core intermediate the backsheet and the topsheet. The topsheet can have an aperture for communicating fecal matter from the wearer to the void space. The spacer can be joined to one of the topsheet, backsheet, or absorbent core.

The spacer has a flexible outer cover, and a plurality of discrete, unconnected elements enclosed in the outer cover. Each of the discrete elements is capable of motion relative to other discrete elements within the outer cover, such as may occur when the spacer is subjected to flexural loading. The spacer can thereby maintain a minimum spacer thickness and void space height under compressive loading, while plastically deforming in response to flexural loading, or bending, about any axis. The spacer is preferably registered with the aperture in the topsheet.

BRIEF DESCRIPTION OF THE DRAWINGS

While the Specification concludes with claims particularly pointing out and distinctly claiming the present invention, it is believed the same will be better understood from the following description taken in conjunction with the associated drawings in which like reference numerals represent the same component and:

DETAILED DESCRIPTION OF THE INVENTION

Figure 1:
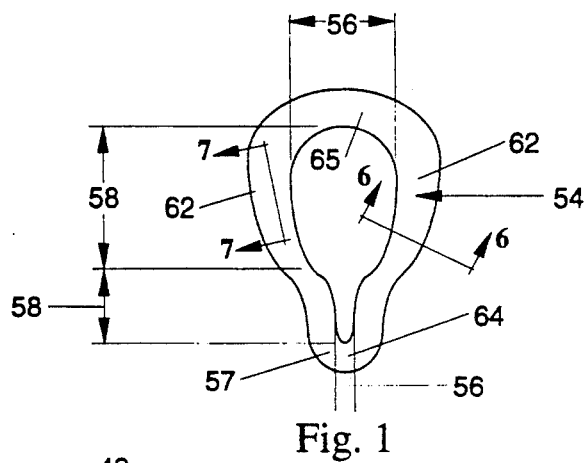
FIG. 1 is a top plan view of a spacer and, according to one embodiment of the present invention, having a shape comprising a closed figure.
Figure 2:
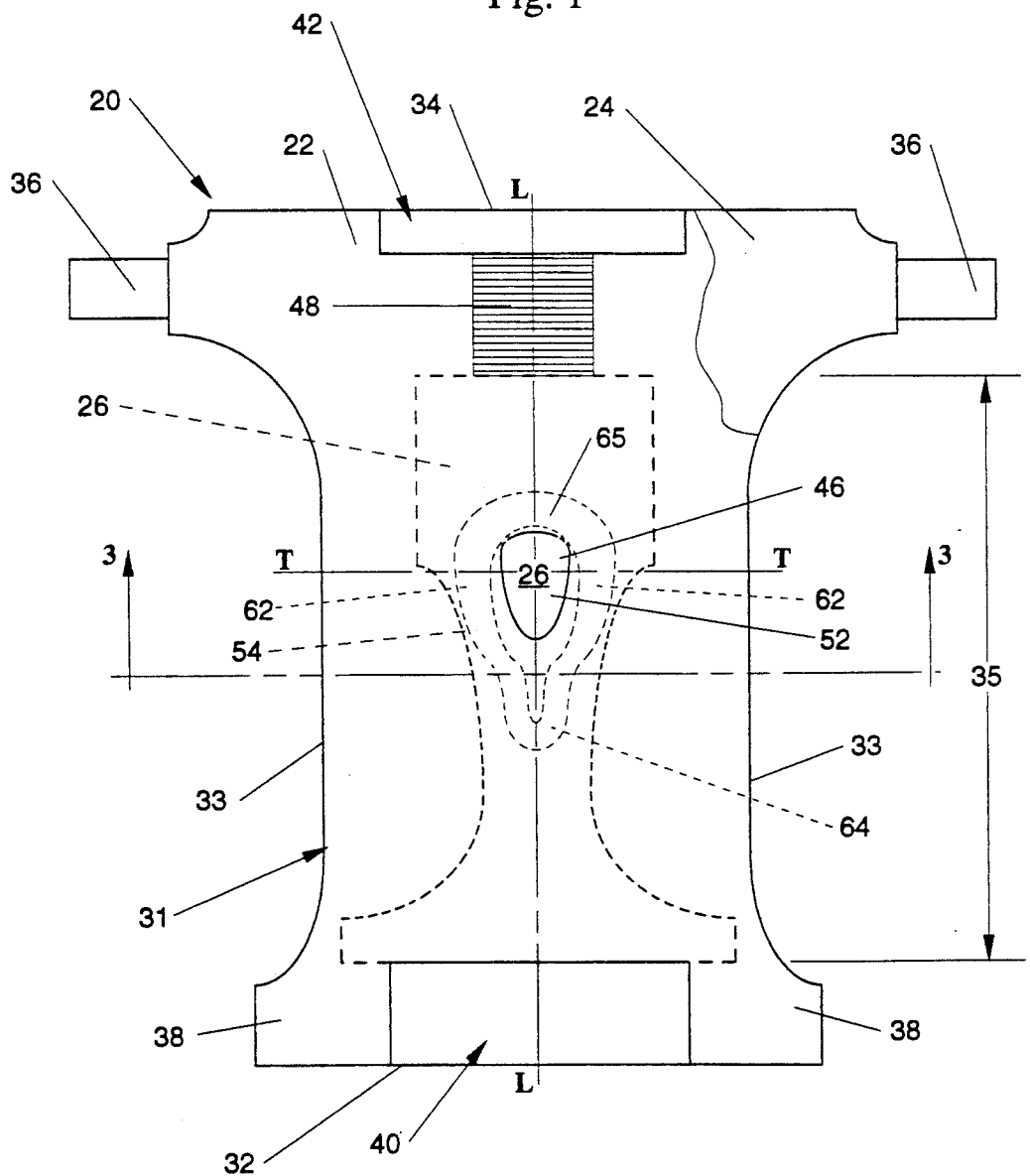
FIG. 2 is a top plan view of a disposable absorbent article shown partially in cutaway and incorporating the spacer of FIG. 1 and an absorbent core in phantom.

Referring to FIGS. 1 and 2, a spacer 54 for use in an absorbent article 20 is shown. A "spacer" refers to a component of a disposable absorbent article 20 which separates two other components of the disposable absorbent article 20 to maintain a desired clearance, or void space, between such components. In particular, the spacer 54 can form a void space for receipt of fecal matter.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted, or otherwise disposed of in an environmentally compatible manner).

A preferred disposable absorbent article 20 according to the present invention comprises a diaper. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, and the like.

The disposable absorbent article 20 comprises a liquid pervious topsheet 22, a liquid impervious backsheet 24, and an absorbent core 26 intermediate the topsheet 22 and the backsheet 24. The topsheet 22 and the backsheet 24 are at least partially peripherally joined to ensure the absorbent core 26 is held in the desired position. As further described in reference to FIG. 4, the absorbent core 26 may comprise two layers, an upper layer 26U juxtaposed with the topsheet 22 and a lower layer 26L juxtaposed with the backsheet 24.

Figure 3:
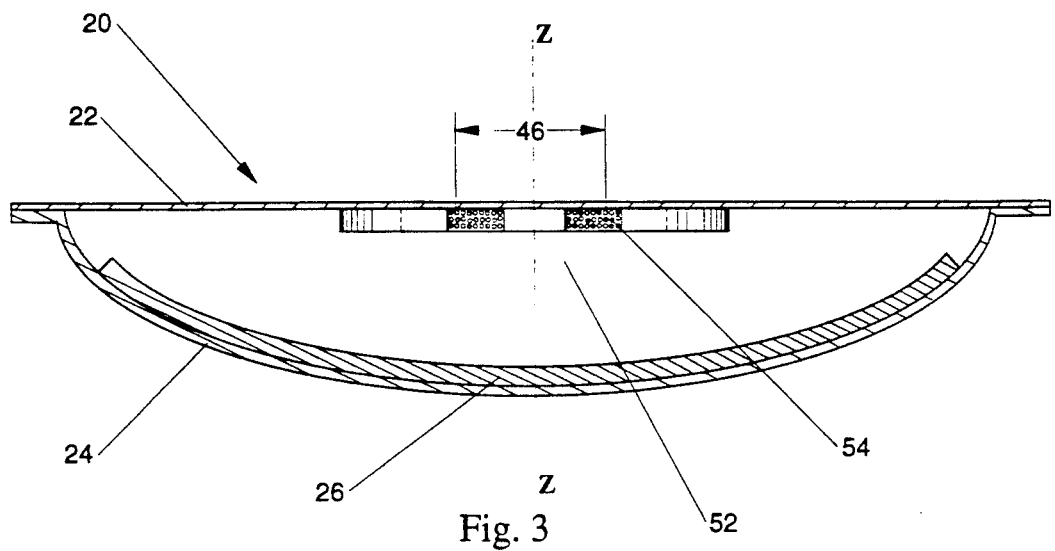
FIG. 3 is a vertical sectional view taken along line 3—3 of FIG. 2, with the spacer joined to a topsheet.
Figure 4:
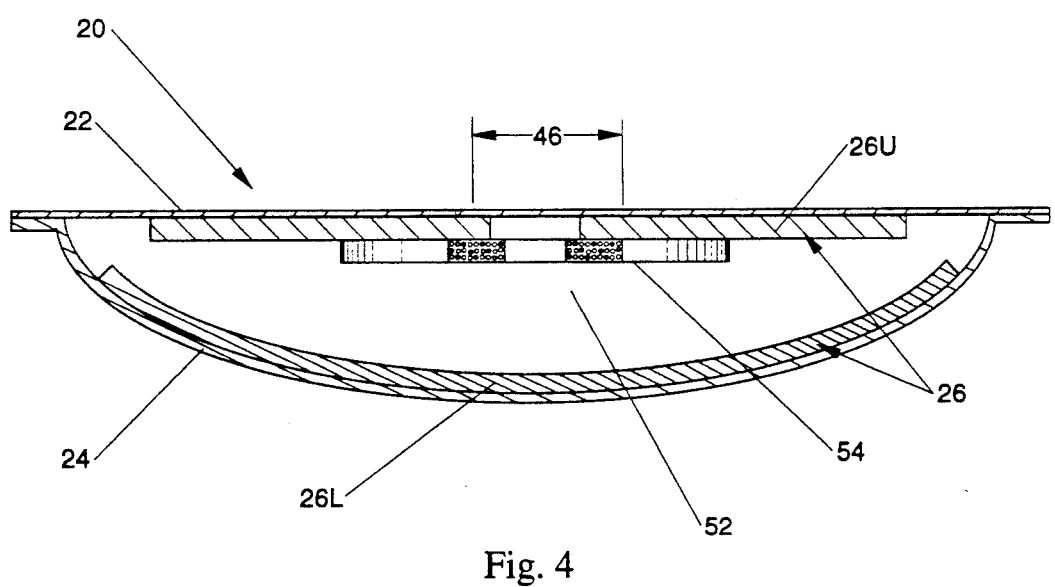
FIG. 4 is a vertical sectional view of an alternative embodiment of a disposable absorbent article having an upper absorbent core layer and a lower absorbent core layer, with the spacer positioned between the upper and lower absorbent core layers and joined to the upper absorbent core layer.

As illustrated in FIG. 3, the disposable absorbent article 20 according to the present invention may further comprise a spacer 54 disposed between the underside of the topsheet 22 and the backsheet 24 and preferably disposed between the underside of the topsheet 22 and the absorbent core 26. Alternatively, as illustrated in FIG. 4, the spacer 54 is disposed between the underside of the upper layer 26U of the absorbent core 26 and the lower layer 26L of the absorbent core 26.

The disposable absorbent article 20 shown in FIG. 2 may further comprise elastic leg cuffs and/or barrier leg cuffs to prevent leakage of body exudates through the leg openings of the disposable absorbent article 20 while it is worn. A disposable absorbent article 20 according to the present invention preferably further comprises an elastic waistband to provide for improved fit about the waist of the wearer. For clarity, the elastic leg cuffs, barrier leg cuffs, and elastic waistband are omitted from the figures. However, if it is desired to incorporate such components into the disposable absorbent article 20, reference is made to the following commonly assigned U.S. Patents which are incorporated herein by reference: U.S. Pat. No. 3,860,003 issued Jan. 14, 1975 to Buell and U.S. Pat. No. 4,081,301 issued Mar. 28, 1978 to Buell which disclose a method and apparatus for applying elastic strands to a disposable absorbent article 20 to make leg cuffs; U.S Pat. No. 4,909,803 issued Mar. 20, 1990 to Aziz et al. which shows how to incorporate barrier leg cuffs into a disposable absorbent article 20; U.S. Pat. No. 4,695,278 issued Sep. 22, 1987 to Lawson which discloses dual cuffs; U.S. Pat. No. 4,515,595 issued May 17, 1985 to Kievit which discloses an elasticized waistband; and U.S. Pat. No. 4,816,025 issued Mar. 28, 1989 to Foreman which discloses how to make a suitable waistband for a disposable absorbent article 20.

A disposable absorbent article 20 according to the present invention may further comprise adhesive tape fasteners 36 juxtaposed with the rear portion 42 and a landing member 38 juxtaposed with the front portion 40 of the disposable absorbent article 20 to conveniently secure the disposable absorbent article 20 about the waist of the wearer. U.S. Pat. No. 3,848,594 issued Nov. 19, 1974 to Buell and U.S. Reissue Patent B1 4,662,875 reissued May 5, 1987 to Hirotsu et al . disclose how to make and , incorporate adhesive tape fasteners 36 into a disposable absorbent article 20, and are incorporated herein by reference.

FIG. 2 illustrates a disposable absorbent article 20 according to the present invention laid out in a flat state having no elastic induced contraction. The topsheet 22 and the backsheet 24 generally define the periphery 31 of the disposable absorbent article 20. The periphery 31 is the outer perimeter and greatest extent of the disposable absorbent article 20. The periphery 31 comprises a front waist margin 32, a rear waist margin 34, and two longitudinal side margins 33.

The front waist margin 32 and rear waist margin 34 are those portions of the disposable absorbent article 20 which, when worn, encircle the waist of the wearer and are generally at the highest elevation of the disposable absorbent article 20 when the wearer is in the standing position. The longitudinal side margins 33 are those portions of the periphery 31 of the disposable absorbent article 20 which connect the front and rear waist margins 32 and 34. The crotch region 35 of the disposable absorbent article 20 is that portion of the disposable absorbent article 20 which is disposed between the front waist margin 32 and rear waist margin 34 and which, when worn, is typically between the legs of the wearer.

As used herein, the "longitudinal" dimension, direction or axis of the disposable absorbent article 20 is that dimension, direction or axis LL which is aligned front to back with respect to the wearer as the disposable absorbent article 20 is worn. The longitudinal axes LL of the spacer 54 and the disposable absorbent article 20 are preferably coincident when the spacer 54 is incorporated into the disposable absorbent article 20.

The "transverse" dimension, direction or axis of the disposable absorbent article 20 is orthogonal the longitudinal direction and sideways aligned as the disposable absorbent article 20 is worn. The transverse axis TT divides the disposable absorbent article 20 into front and rear portions 40 and 42, corresponding in position to the respective front and rear waist margins 32 and 34. The "Z-direction" is orthogonal with respect to both the longitudinal and transverse directions, and does not lie within the plane of the disposable absorbent article 20 or within the plane of the spacer 54.

The embodiment described herein is suitable for a wearer weighing about 7.3 kilograms to about 12.2 kilograms (16 to 27 pounds) and having ischia bones spaced about 3.0 centimeters to about 7.6 centimeters (1.2 to 3.0 inches) apart. It will be understood that if the spacer 54 and disposable absorbent article 20 are intended for use with smaller or larger sized wearers, including adults, the disposable absorbent article 20 and spacer 54 will have to be scaled accordingly.

The spacer 54 sized to fit the aforementioned range of wearers should have a thickness t (FIG. 6) in the Z-direction of at least 0.64 centimeters (0.25 inch). The spacer 54 illustrated in FIG. 1 may have an overall longitudinal dimension of about 8.9 to about 11.8 centimeters (3.5 to 4.6 inches) and a transverse opening of about 1.9 centimeters (0.75 inches). Such a spacer 54 may also have an overall transverse dimension at the perimeter of the smaller end of the spacer 54 intended for disposition towards the front waist margin 32 of the disposable absorbent article 20 of about 4.9 centimeters (1.93 inches) and an overall transverse dimension at the perimeter of the larger end of the spacer 54 intended to be oriented towards the rear waist margin 34 of about 9.53 centimeters (3.75 inches). This spacer 54 may have a radial thickness ranging from about 1.14 centimeters (0.45 inches) at the smaller end of the spacer 54 to a radial thickness of about 2.8 centimeters (1.1 inches) at the larger end of the spacer 54.

A disposable absorbent article 20 sized to fit the aforementioned range of wearers may be made having a topsheet 22 with a longitudinal dimension of about 43.8 centimeters (17.25 inches) and a backsheet 24 having a longitudinal dimension of about 46.4 centimeters (18.25 inches). As illustrated in FIG. 3, the difference in longitudinal dimension between the topsheet 22 and the backsheet 24 foreshortens the topsheet 22 relative to the backsheet 24 creating a void space 52 therebetween, even when a absorbent core 26 is interposed between the topsheet 22 and the backsheet 24. As used herein, a "void space" is a cavity intermediate the topsheet 22 and the backsheet 24, which cavity is sized to accept fecal material. The topsheet 22 and backsheet 24 according to the present invention have a transverse dimension, at the crotch region 35, of about 15.9 centimeters (6.25 inches) and about 21.3 centimeters (8.4 inches) respectively.

The elements of the disposable absorbent article 20 may be assembled in any variety of configurations well known to one skilled in the art. Preferred configurations are described in commonly assigned U.S. Pat. No. 3,860,003 issued Jan. 14, 1975 to Buell, and the aforementioned commonly assigned U.S. Pat. No. 4,909,803 issued Mar. 20, 1990 to Aziz et al., which patents are incorporated herein by reference for the purpose of disclosing well known and preferred disposable absorbent article 20 configurations. In an even more preferred embodiment the configuration of the disposable absorbent article 20 conforms to the teachings of U.S. Pat. No. 5,151,092 issued to Buell et al on Sep. 29, 1992, which patent is incorporated herein by reference.

Examining the components of the disposable absorbent article 20 in more detail, the topsheet 22 and backsheet 24 are generally coextensive and at least partially peripherally joined together as noted above. As used herein the term "joined" refers to the condition where a first member or component is affixed or connected to a second member or component, either directly, or indirectly where the first member or component is affixed or connected to an intermediate member or component which in turn is affixed or connected to the second member or component.

The topsheet 22 and backsheet 24 may be joined by any means well known in the art, such as adhesive bonding or heat sealing. A particularly preferred method of joining the topsheet 22 and backsheet 24 is using hot-melt adhesive such as manufactured by Century Adhesives, Inc. of Columbus, Ohio and marketed as Century 5227 or HL1258 adhesive sold by the H. B. Fuller Company of St. Paul, Minn. In a particularly preferred embodiment, adhesive joining is accomplished by longitudinally oriented adhesive bands or spirals.

As used herein, the term "absorbent core" refers to any component of the disposable absorbent article 20 used for absorbing and retaining body exudates. The absorbent core 26 may have opposed major faces and may, if desired, be encased by one or more layers of tissue (not shown), or may be coated with a release agent to reduce friction against the fecal material.

The tissue layer, if present, improves the tensile strength of the absorbent core 26 and reduces its tendency to split or clump when wetted. The tissue layer may further improve transverse wicking of fluids and more evenly distribute absorbed liquids throughout the absorbent core 26. A tissue layer having a basis weight of approximately 16 grams per square meter (10 pounds per 3,000 square feet) and an air permeability of approximately 30 cubic meters per minute per square meter (100 cubic feet per minute per square foot) and a differential pressure of 13 millimeters of water (0.5 inch of water) has been found to work well.

The absorbent core 26 may be made from a variety of commonly used materials such as comminuted wood pulp, typically referred to as airfelt. If desired, the absorbent core 26 may further contain absorbent gelling materials as is commonly used in the art. In particular, the absorbent core 26 may be made in accordance with the teachings of commonly assigned U.S. Pat. No. 4,610,678 issued Sep. 9, 1986 to Weisman et al., which patent is incorporated herein by reference for the purpose of showing how to make an absorbent core 26 suitable for use with the present invention. Absorbent gelling materials made in accordance with commonly assigned U.S. Patent Re. 32,649 issued Apr. 19, 1988 to Brandt et al . have been found suitable for use in a disposable absorbent article 20 according to the present invention.

If desired, in a particularly preferred embodiment the lower layer 26L of the absorbent core 26 may have discrete storage and acquisition zones. The storage zone has a higher average density and higher average basis weight than the acquisition zone, so that the acquisition zone may effectively and efficiently acquire rapidly discharged liquids and transport the same to the storage zone for long term containment. Such a lower layer 26L may be made in accordance with the teachings of commonly assigned U.S. Pat. No. 4,834,735 issued May 30, 1989 to Alemany et al., which patent is incorporated herein by reference for the purpose of showing how to make a particularly preferred lower layer 26L of the absorbent core 26. One suitable absorbent core 26 material is a fibrous absorbent gelling material such as is sold under the tradename Fibersorb by the Atlantic Richfield Company of Los Angeles, Calif.

As illustrated in FIG. 4, the absorbent core 26 may comprise two separate layers, an upper layer 26U which is joined to the underside of the topsheet 22 and a lower layer 26L which is joined to the upper side of the backsheet 24. The absorbent core 26 has longitudinal and transverse dimensions generally less than those of the topsheet 22 and the backsheet 24. The lower layer 26L of the absorbent core 26 may be made of a variety of sizes and shapes, such as rectangular or hourglass. The upper layer 26U of the absorbent core 26 generally matches the shape of the rear portion 42 of the topsheet 22. Of course, a single layer absorbent core 26, as is well known in the art may be utilized.

The upper and lower layers 26U and 26L of the absorbent core 26 may be adhesively joined to the topsheet 22 and backsheet 24, respectively, or joined thereto by any attachment means well known in the art. Particularly preferred attachment means are adhesive spirals and longitudinal and transverse bands of adhesive. Particularly preferred types of adhesive are manufactured by Century Adhesives, Inc. of Columbus, Ohio as Century 5227, HL-1258 Adhesive sold by the H. B. Fuller Company of St. Paul, Minn. and XPO-9-035 adhesive manufactured by the Minnesota Mining and Manufacturing Company of St. Paul, Minn.

Preferably, the lower layer 26L of the absorbent core 26 extends the entire longitudinal dimension of the disposable absorbent article 20 between the front waist margin 32 and the rear waist margin 34, but does not intrude into either the front waist margin 32 or the rear waist margin 34. The upper layer 26U of the absorbent core 26 need only be present in the rear portion 42 of the disposable absorbent article 20.

One opposed face of the lower layer 26L of the absorbent core 26 is oriented towards the upper absorbent core 26 layer and the underside of the topsheet 22. The other opposed face of the lower layer 26L of the absorbent core 26 is oriented towards the backsheet 24, and preferably is in contacting relationship therewith. More preferably, the lower layer 26L of the absorbent core 26 is adhesively joined to the backsheet 24.

The upper layer 26U of the absorbent core 26 insulates the wearer from the impression and applied pressures of the spacer 54, discussed below, which occur when the wearer is sitting while wearing the disposable absorbent article 20. For this reason, the upper layer 26U of the absorbent core 26 should be present in at least the rear portion 42 of the disposable absorbent article 20 and particularly, be present between the rear waist margin 32 and the aperture 46. It is not necessary that the upper layer 26U of the absorbent core 26 be present in the front portion 40 of the disposable absorbent article 20, because in a preferred embodiment the absorbent core 26 has sufficient absorptive capacity without requiring an upper layer 26U of the absorbent core 26 in the front portion 40 of the disposable absorbent article 20.

Preferably, the exposed faces of the upper layer 26U and the lower layer 26L (those faces not attached to the topsheet 22 or the backsheet 24 respectively) are well defined and do not intrude into the void space 52. Intrusion of a significant quantity of loose fibers into the void space 52 from the absorbent core 26 could interrupt (if not block) the transport of fecal material in the longitudinal direction, and prevent the isolation of such fecal material from the skin of the wearer.

Referring back to FIG. 2, the "topsheet" refers to any liquid pervious facing of the disposable absorbent article 20 which contacts the skin of the wearer while the disposable absorbent article 20 is worn and prevents substantial contact of the absorbent core 26 with the skin of the wearer. The topsheet 22 is preferably compliant, tactilely pleasant and non-irritating to the skin of the wearer. Preferably the topsheet 22 is treated to be hydrophilic, to more readily transport body exudates to the absorbent core 26.

A suitable topsheet 22 may be manufactured from materials such as porous foams, apertured plastic films, natural fibers (e.g. wood fibers or cotton fibers), synthetic fibers (e.g. polyester or polypropylene fibers) or a combination of the foregoing. A particularly preferred topsheet 22 comprises polypropylene fibers having a denier of about 2.2 and a length of about 15.9 millimeters (0.62 inches). The topsheet 22 may be manufactured according to a number of techniques. For example, the topsheet 22 may be a nonwoven web of fibers spunbonded, carded, wet-laid, meltblown, hydroentangled, combinations of the above, or the like.

A particularly preferred topsheet 22 is carded and thermally bonded and has a basis weight of about 18 to about 25 grams per square meter. A suitable topsheet 22 is marketed by Veratec, Inc., Division of International Paper Company of Walpole, Massachusetts under the designation P-8.

Preferably, the topsheet 22 has an elastic panel 48 intermediate the transverse axis and the rear waist margin 34. The elastic panel 48 maintains the topsheet 22 close to the wearer's skin, and helps to maintain registration of the aperture 46 with the anal opening. The elastic panel 48 may be incorporated according to the teachings of commonly assigned U.S. Pat. No. 5,032,120 issued Jul. 16, 1991 to Freeland et al., which patent is incorporated herein by reference for the purpose of showing how to make material suitable for the elastic panel 48 and incorporate the elastic panel 48 into the topsheet 22.

If present, the elastic panel 48 is preferably transversely centered on the longitudinal axis, and may transversely extend between the entire longitudinal side margins of the disposable absorbent article 20 or may only be about 3.8 to about 4.5 centimeters (1.5 to 1.8 inches) in width. The elastic panel 48 may longitudinally extend from the rear waist margin 34 to the aperture 46. The elastic panel 48 is preferably about 1.3 centimeters (0.5 inches) in longitudinal dimension in an unstretched condition, and may be extended about 300 percent to a longitudinal dimension of about 5.1 centimeters (2.0 inches) when incorporated into the topsheet 22.

The material comprising the elastic panel 48 should extend about 200 percent under about 6 to about 8 grams of applied loading per 0.03 millimeters (0.001 inches) of thickness per unit centimeter (0.4 inches) of width. A particularly preferred elastic panel 48 may be made according to the teachings of commonly assigned U.S. Pat. No. 5,037,416 issued Aug. 6, 1991 to Allen et al., which patent is incorporated herein by reference for the purpose of illustrating a particularly preferred material of construction for the elastic panel 48.

The pervious topsheet 22 further comprises an aperture 46 centered on the longitudinal axis LL. The aperture 46 may be of any shape desired with a suitable shape being an oval having a longitudinal dimension of about 5.1 centimeters (2.0 inches) and a transverse dimension of about 3.8 centimeters (1.5 inches). The rearwardmost edge of the aperture 46 is disposed at least about 15.2 centimeters (6.0 inches), and preferably about 17.8 centimeters (7.0 inches) to about 21.6 centimeters (8.5 inches) from the rear edge of the disposable absorbent article 20 while it is worn. Alternatively, the aperture 46 may be circular, having a dimension of about 4.13 centimeters (1.625 inches), and centered about 22.38 centimeters (8.813 inches) from the rear waist margin 34. Alternatively, the aperture 46 may be sized and shaped to match the inside of the spacer 54 according to the present invention. Preferably, the spacer 54 is registered with the aperture 46.

The aperture 46 provides a passageway for the communication of fecal material from the anal opening through the topsheet 22 into the void space 52. Preferably absorbent gelling materials are not registered with the aperture 46, so that gel-blocking does not occur when large volume urine loading occurs. Gel-blocking may cause the lower layer 26L to block the void space 52 and interrupt the transport of fecal material towards the rear waist margin 34.

The backsheet 24 is impervious to fluids, such as urine, and prevents fluids absorbed by and contained in the absorbent core 26 from wetting undergarments, clothing and bedding. As used herein the "backsheet" refers to any barrier disposed outwardly of the absorbent core 26 as the disposable absorbent article 20 is worn and which contains absorbed liquids within the disposable absorbent article 20. The backsheet 24 is preferably manufactured from a thin plastic film, although other flexible liquid impervious materials may also be used. As used herein, the term "flexible" refers to materials which are compliant and will readily conform to the general shape and contours of the human body.

The backsheet 24 may be a polyolefinic film, such as polyethylene, having a thickness of about 0.01 millimeters to about 0.051 millimeters (0.0005 to 0.002 inches). If desired, the backsheet 24 may be embossed or matte finished to provide a cloth-like appearance and may be breathable. A suitable backsheet 24 can be made from a blend of about 45 to 90 percent linear low density polyethylene and about 10 to 55 percent polypropylene. Exemplary backsheet 24 films are sold by Tredegar Industries, Inc. of Terre Haute, Indiana under the designation RR8220 blend for blown films and RR5475 blend for cast films.

Referring again to FIGS. 1 and 2, the spacer 54 can have a shape comprising a generally closed figure. The closed figure shape shown in FIGS. 1 and 2 provides the spacer 54 longitudinally disposed so that the end having the small radius of curvature and a smaller lateral span 56 is oriented towards the front waist margin 32 and the end having the larger radius of curvature and the greater transverse span 56 is oriented towards the rear waist margin 34.

This "keyhole" shape shown in FIGS. 1 and 2 comfortably accommodates the thighs of the wearer, due to the smaller transverse span 56 at the end of the spacer 54 having the smaller radius of curvature. The closed figure spacer 54 of FIGS. 1 and 2 includes laterally spaced apart longitudinally extending portions 62, where portions 62 are registered with the aperture 46. The spacer 54 shown in FIGS. 1 and 2 also includes a laterally extending portion 64 positioned forward of the aperture 46 and connecting the longitudinally extending portions 62, and a laterally extending portion 65 positioned rearward of the aperture 46. Laterally extending portion 64 is positioned intermediate the front waist margin 32 and the aperture 46. Laterally extending portion 65 is positioned intermediate the rear waist margin 34 and the aperture 46. Other spacer shapes comprising a generally closed figure can include, but are not limited to, circles, ovals, and polygons.

Figure 5:
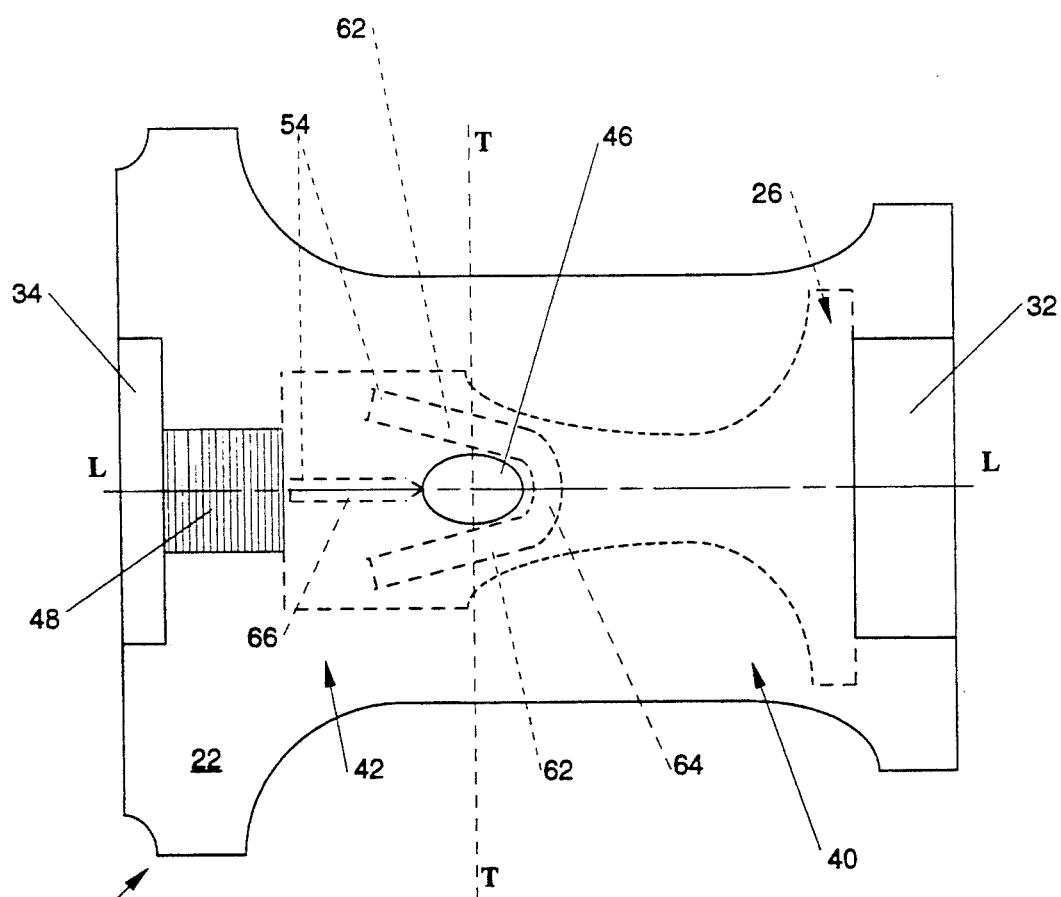
FIG. 5 is a top plan view of an alternate embodiment of the disposable article wherein the spacer shape comprises an open figure concave towards the rear waist margin of the absorbent article.

Alternatively, the spacer 54 can have a shape comprising an open figure, such as shown in FIG. 5. A laterally extending portion 64 can connect longitudinally extending portions 62 to form a generally U-shaped configuration that opens rearwardly. Where the laterally extending spacer portion 64 is omitted, the spacer 54 in FIG. 5 can comprise two separate longitudinally extending portions 62. A separate central spacer portion 66 can be disposed in the rear portion 42 of the disposable absorbent article parallel and coincident to the longitudinal centerline LL. The central spacer portion 66 can reduce sagging of the upper layer 26U of the absorbent core into the void space 52.

It is desirable that the spacer 54 be registered with the aperture 46. A spacer 54 registered with the aperture 46 spaces a part of the absorbent article 20 underlying the aperture 46, such as a part of the absorbent core 26 or backsheet 24, away from the wearer's body. Body exudates, such as fecal matter, can thereby pass through the aperture 46 and into void space 52.

Figure 6:
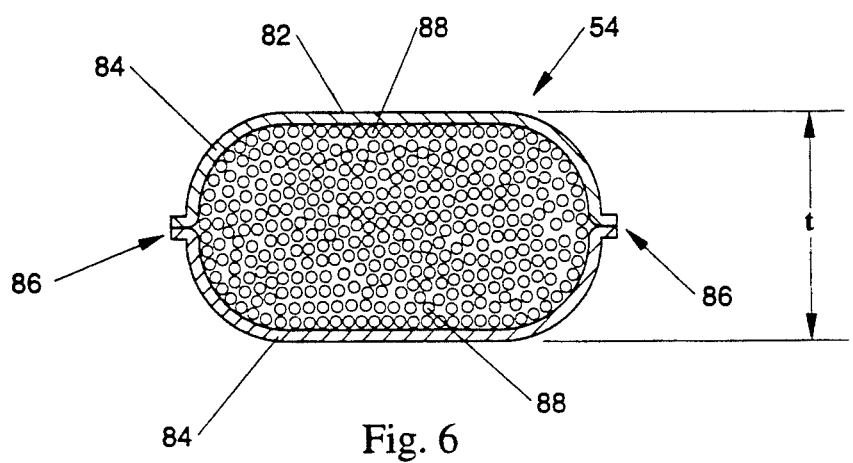
FIG. 6 is a vertical sectional view taken along line 6—6 of FIG. 1.

Referring to the cross-sectional view of FIG. 6, a spacer 54 according to the present invention comprises an outer cover 82, and a plurality of discrete elements 88 enclosed in the outer cover 82. In the embodiment shown the outer cover 82 comprises a pair of cover portions 84 joined at outer cover seams 86. Alternatively, a single cover portion 84 can have ends joined at a single seam. In yet another embodiment, the outer cover 82 can comprise an outer cover portion 84 joined to the topsheet 22, backsheet 24, or absorbent core 26, with the discrete elements 88 disposed between the outer cover portion 84 and the topsheet 22, backsheet 24, or absorbent core 26. Discrete elements 88 are disposed in the outer cover 82 such that discrete elements 88 are free to move relative to one another within the outer cover 82. Relative motion of discrete elements 88 within outer cover 82 allows the spacer 54 to deform plastically in response to flexural loading about any one of three mutually perpendicular axes. At the same time, the outer cover 82 prevents unrestricted spreading of the discrete elements 88, so that the spacer 54 can maintain a Z direction thickness t under compressive loading. Thickness t is shown in FIG. 6.

The term "flexural loading" refers to applied forces, applied displacements, or a combination of applied forces and displacements that result in bending of a structure. Applied forces are understood to include force couples, or moments. By "flexural loading about an axis" it is meant the flexural loading results in bending of a structure about the specified axis. For example, a structure aligned with the longitudinal axis LL and subjected to flexural loading about the transverse axis TT would bend about the transverse axis TT. That is, the structure would deform in the Z direction as a function of position along the longitudinal axis LL.

By "plastically deform" as used herein, it is meant that, upon removal of the loading causing the deformation, the loaded structure remains in substantially the deformed configuration and does not partially or totally regain its original undeformed shape. By "plastically-deform" as used herein it is also meant that, upon deformation of the structure, no internal restoring forces tending to resist deformation and restore the structure to its original configuration are generated in the structure.

Conventional spacers exhibit flexural rigidity in response to flexural loading. These spacers develop internal forces which resist bending and which tend to restore the spacer to its original undeformed shape. This characteristic of conventional spacers can be understood by reference to the cross-sectional stress distribution in a beam undergoing bending.

Beams subjected to flexural loading have a cross-sectional stress distribution characterized by a line, referred to as the neutral axis, and having no bending stress. The neutral axis separates regions of tensile and compressive bending stresses. Together, these tensile and compressive stresses form an internal force couple which resists bending of the beam. It is desirable that spacers in disposable absorbent articles have a minimum thickness in order to maintain a void space. However, as the thickness of a beam increases, the flexural rigidity of the beam also increases. A discussion of flexure of beams and the resulting tensile and compressive stress distribution in beam cross-sections can be found in Mechanics of Materials, Second Edition, by E.P. Popov, at pages 119–140.

Thus, conventional spacers require a trade-off between void space height and flexural rigidity. Increased void space height is desirable for increased BM containment volume. However, an increased spacer thickness, which is required to maintain an increased void space height, also increases the flexural rigidity of the spacer.

The spacers 54 of the present invention can provide increased void space height without this corresponding increase in flexural rigidity. The spacers 54 of the present invention are not able to develop tensile bending stresses in response to flexural loading because the discrete elements 88 are not connected, and can move relative to one another within the outer cover 82. As a result, there is no load path for tensile stresses in the spacer 54. Therefore, the spacer 54 cannot develop an internal force couple to resist bending, and the spacer 54 plastically deforms in response to flexural loading. In addition, the discrete elements can move relative to one another in any direction. Therefore, the spacer 54 can plastically deform in response to flexural loading about any axis.

The discrete elements 88 preferably have a generally rounded surface to promote relative motion of adjacent discrete elements 88. More preferably, the discrete elements 88 have a generally spherical shape to permit adjacent discrete elements 88 to move freely in any direction with respect to other discrete elements 88.

The discrete elements 88 can comprise any absorbent or non-absorbent material which resist compressive loading. Preferably, the discrete elements 88 are made of a material that does not lose its stiffness or collapse when wetted.

In a preferred embodiment, the discrete elements 88 comprise generally spherically shaped expanded polystyrene beads having a diameter between 0.254 centimeter (0.10 inch) and 0.64 centimeter (0.25 inch). Suitable expanded polystyrene beads are commercially available as Prepuffed Beads from Southern Ohio Foam of Lebanon, Ohio, and as Pelspan expanded polystyrene beads from the Snow Craft Company of Garden City Park, N.Y. In an alternative embodiment, the discrete elements 88 can comprise generally ovoid shaped polypropylene pellets available as Poly-Pellets from the Fairfield Processing Corporation of Danbury, Conn.

The outer cover 82 should be flexible. In particular, the outer cover 82 should be made of a material that acts only as a membrane, and which does not support bending stresses across its thickness.

The outer cover 82 can comprise a liquid pervious material. A liquid pervious outer cover 82 may be manufactured from a wide range of materials, such as apertured plastic films, porous foams, reticulated foams, or woven or nonwoven webs of natural fibers (e.g., wood or cotton fibers), synthetic fibers (e.g., polyester or polypropylene fibers), or a combination of natural and synthetic fibers. There are a number of manufacturing techniques which may be used to manufacture the outer cover 82. For example, the outer cover 82 may be a nonwoven web of fibers spunbonded, carded, wet-laid, meltblown, hydroentangled, or a combination of the above.

The outer cover 82 can comprise the same material from which the topsheet 24 is made. For example, the outer cover can comprise the web of staple length polypropylene fibers manufactured under the designation P-8 by Veratec, Inc., discussed above. Another suitable outer cover 82 comprises a hydroentangled or spunlaced apertured nonwoven having a basis weight of at least 0.0036 grams per square centimeter (30 grams per square yard), and preferably about 0.0060 grams per square centimeter (50 grams per square yard). Such a material is commercially available as Sontara from the E. I. DuPont de Nemours and Company of Wilmington, Del. The outer cover 82 can also comprise a web of spun laid thermal discrete bonded polypropylene fibers with a fiber denier in the 2 to 2.5 denier range and a basis weight of between 0.0017 gram per square centimeter (0.5 ounce per square yard) and 0.0030 gram per square centimeter (0.9 ounce per square yard), and preferably about 0.0022 gram per square centimeter (0.65 ounce per square yard). Such a material is available from Fiberweb Corporation of Simpsonville, South Carolina as Celestra Unicorn 0.65 SLP 09U (untreated)/ 0.65 SSP 09U (treated to be hydrophilic).

In some applications it may be desirable that outer cover 82 comprise a liquid impervious material. For instance, it may be desirable to have spacer 54 act as a gasket to prevent forward flow of liquid or "runny" fecal material passing through aperture 46. A suitable fluid impervious material for forming outer cover 82 can comprise the same material from which the backsheet 26 is formed. For example, the outer cover 82 can comprise a polyolefinic film, such as polyethylene having a thickness of about 0.01 millimeters to about 0.051 millimeters (0.0005 to 0.002 inches). Exemplary fluid impervious materials from which outer cover 82 can be made include: plastic films designated RR8220 and RR5475 (0.025 millimeter thick) sold by Tredegar Industries, Inc. of Terre Haute, Indiana; and a plastic film sold by the Clopay Corporation of Cincinnati, Ohio under the designation P18-1401, with a thickness of 0.018 to 0.030 millimeters (0.0007 to 0.0012 inch).

The spacer 54 can be adhesively joined to the topsheet 22, as shown in FIG. 3, or adhesively joined to the absorbent core 26, as shown in FIG. 4. In other embodiments, the spacer 54 can be adhesively joined to the backsheet 24. One suitable adhesive for joining the spacer 54 to the topsheet 22, the absorbent core 26, or the backsheet 24 includes a hot-melt adhesive such as that manufactured by Century Adhesives, Inc. of Columbus Ohio and marketed as Century 5227, or HL1258 adhesive sold by the H.B. Fuller Company of St. Paul, Minnesota. Other methods of joining the spacer 54 to the absorbent article 20 include heat sealing and ultrasonic bonding. The pair of cover portions 84 can be adhesively joined at outer cover seams 86 with the adhesives listed above.

As explained above, spacer 54 plastically deforms in response to flexural loading. It is also desirable that the spacer 54 maintain a sufficient thickness t when loaded by the weight of the wearer of the absorbent article 20. Preferably, the spacer 54 maintains a thickness of at least 0.64 centimeters (0.25 inch) when loaded by the weight of the wearer.

The magnitude and manner of loading of the spacer will vary depending on a number of factors, such as the wearer's size and the geometry of the absorbent article 20 and the spacer 54. The loading of the spacer 54 may be fairly uniform, but is typically highly localized, being concentrated at the ischia bones of the wearer. Therefore, it is not possible to predict the exact loading conditions to which spacer 54 will be subjected in an absorbent article 20.

For the purposes of the present invention, it is desirable that the spacer 54 maintain a thickness t of 0.64 centimeters (0.25 inch) under a compressive loading of 350 kilograms per square meter (0.5 pounds per square inch), where the compressive loading has a circular area of application, or footprint, of about 6.45 square centimeters (1.0 square inch). It is to be understood that the above loading characteristics are not meant to represent the actual loading conditions in a particular absorbent article 20, but are intended to be used to describe the present invention.

Figure 7:
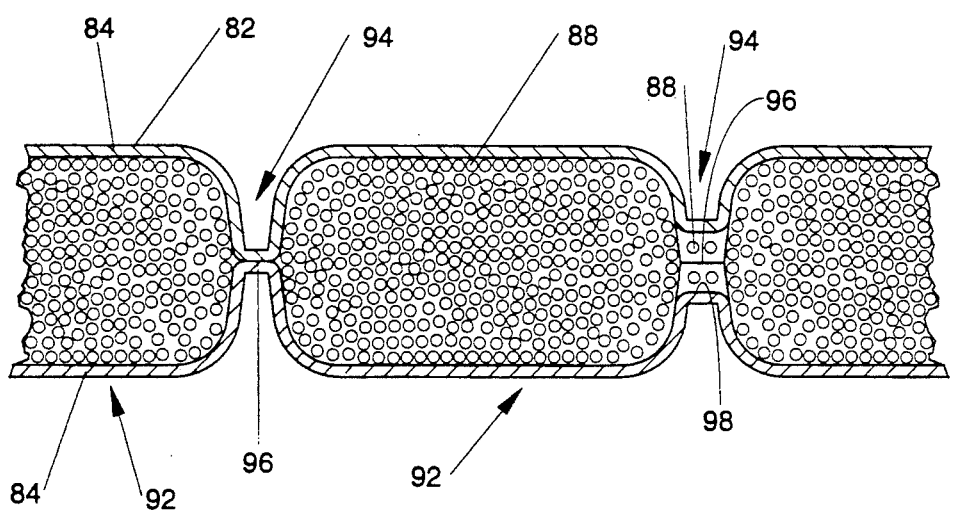
FIG. 7 is a vertical sectional view taken along line 7—7 of FIG. 1 showing a spacer having compartments.

In one alternative embodiment, the spacer 54 can comprise separate compartments 92 as shown in FIG. 7. The compartments 92 can prevent accumulation of the discrete elements 88 in one portion of the spacer 54 and a concurrent sparsity of elements 88 in other portions of the spacer 54. Such a shifting of the discrete elements 88 is generally undesirable because a portion of the spacer 54 having few or no discrete elements 88 cannot maintain a Z-direction thickness t under compressive loading.

In FIG. 7, the compartments 92 are formed by bonding together cover portions 84 at a plurality of seams 96 to form spaced apart compartment ends 94. The seams 96 can extend across the full width of the compartments 92. Each compartment end 94 thereby forms a generally radially oriented hinge in the spacer 54, reducing its flexural rigidity in the directions generally normal to the hinge. Alternatively, each seam 96 can extend part way across the width of the compartment 92 to form a passage 98 between interconnected compartments 92. Passages 98 permit limited movement of discrete elements 88 between adjacent compartments 92. In an alternative embodiment, rather than bonding together cover portions 84, the compartment ends 94 can comprise a separate piece attached to and extending intermediate the outer cover portions 84.

Without being limited by theory, it is believed that the ability of the spacer 54 to plastically deform in response to flexural loading and to maintain a thickness t under compressive loading will be affected by the number of discrete elements 88 within the outer cover 82. For instance, where only a small number of discrete elements 88 are enclosed within the outer cover 82, the wearer's weight may cause the discrete elements 88 to spread within the outer cover 82 and reduce the thickness t and void space thickness below the minimum desired value of 0.64 centimeter set forth above.

Conversely, if the discrete elements 88 are packed too tightly within the outer cover 82, the discrete elements 88 will not move freely relative to each other, and the spacer 54 may not plastically deform in response to flexural loads. Instead, the outer cover 82 will carry tensile forces, and the spacer 54 will develop an internal force couple which will resist bending.

The spacer 54 will have a characteristic "packing density" which can be calculated as follows:

$$\text{Packing Density} = V88/V82$$

where $V88$ is the volume of the discrete elements 88 enclosed by outer cover 82, and $V82$ is the volume of the outer cover 82. The volume of the outer cover 82 is measured or calculated without stretching the outer cover 82.

In one embodiment, the packing density should be less than about 60 percent, preferably about 20-50 percent, and more preferably about 20-30 percent. Without being limited by theory, it is believed that a spacer 54 having a packing density at the lower limit of about 20 percent exhibits the lowest flexural rigidity of a spacer 54 which can maintain a thickness of 0.64 centimeters (0.25 inch) under compressive loading of 350 kilograms per square meter (0.5 psi), where the compressive loading has a circular footprint of about 6.45 square centimeters (1.0 square inch). A spacer 54 having a packing density above the upper limit of 60 percent may be excessively stiff.

The packing density can be selectively varied in different portions of the spacer 54, particularly if the spacer 54 includes the separate compartments 92. For example, the packing density can be a relatively high value where the wearer's weight is concentrated, and a relatively low value where maximum flexibility is desired.

Referring to FIGS. 1 and 7, the spacer 54 can have at least a portion of a first compartment 92 having a first relatively high packing density positioned in the longitudinally extending portion 62 corresponding to the location of the wearer's ischia bones. The spacer 54 can have at least a portion of a second compartment 92 with a second relatively low packing density positioned in the laterally extending portion 64 intermediate the aperture 46 and the front waist margin 32. The spacer 54 can have at least a portion of a third compartment 92 with a third packing density intermediate the first and second packing densities positioned in the laterally extending portion 65 intermediate the aperture 46 and the rear waist margin 34.

In yet another embodiment, the desired effective packing density may be achieved by providing a spacer 54 having a packing density greater than 60 percent and an elastically extensible outer cover 82. The term "elastically extensible" means able to be stretched from the free length at least about 50 percent for a period of about 15 seconds and to return to within about 10 percent of the free length within about 5 minutes of release of the forces which cause such elongation. The elastically extensible outer cover 82 can expand upon flexural loading of the spacer 54, providing for movement of the discrete elements 88 relative to each other.

This arrangement provides the advantage that the more tightly packed discrete elements 88 are less likely to spread into a thin layer, and thereby allow the spacer 54 to collapse to less than the 0.635 centimeter (0.25 inch) desired Z direction thickness. Such an elastically extensible outer cover 82 may be made according to the teachings of commonly assigned U.S. Pat. No. 5,037,416 issued Aug. 6, 1991 to Allen et al, which patent is incorporated by reference for the purpose of showing an elastically extensible material for such an outer cover 82. Other suitable materials for use in a spacer 54 having a packing density greater than about 60 percent include fiber nonwoven materials and knitted nylon or Lycra fabrics, such as are disclosed in commonly assigned U.S. Pat. No. 4,990,147 issued Feb. 5, 1991 to Freeland, which patent is incorporated by reference.

Without being limited by theory, it will be understood that the ability of the spacer 54 to plastically deform in response to flexural loading is not unlimited. As the spacer 54 is flexed beyond a certain curvature, or threshold loading level, the outer cover 82 will begin to carry tensile forces, and the spacer 54 will develop an internal force couple which will resist further bending. The level of flexural loading at which the outer cover 82 begins to carry tensile loads will vary depending on a number of factors, including but not limited to, the direction of loading and the packing density.

However, the spacers 54 of the present invention provide the advantage that they plastically deform below a threshold loading level, and become flexurally stiff above the threshold loading level. In contrast, conventional spacers are relatively stiff (and therefore uncomfortable) at low loading levels, and only deform plastically where loading levels are high enough to cause the conventional spacer material to plastically elongate.

It will be apparent that several other modifications and variants may be made by one skilled in the art. All are within the scope and intent of the appended claims.

What is claimed is:

1. A spacer for maintaining a fecal void space in a disposable diaper, the spacer comprising:
   a flexible outer cover; and
   a plurality of discrete elements enclosed in the outer cover, each discreate element relatively movable with respect to other discrete elements within the outer cover;
   the spacer being a generally closed figure having an opening therethrough, whereby fecal material may pass through the opening into the void space of the diaper.

2. The spacer recited in claim 1 wherein the discrete elements have a generally rounded surface.

3. The spacer recited in claim 2 wherein the discrete elements have a generally spherical shape.

4. The spacer recited in claim 3 wherein the discrete elements comprise expanded polystyrene beads.

5. The spacer recited in claim 1 wherein the spacer has a packing density of less than 60 percent.

6. The spacer recited in claim 5 wherein the spacer has a packing density of between 20 and 50 percent.

7. The spacer recited in claim 6 wherein the spacer has a packing density of of between 20 and 30 percent.

8. The spacer recited in claim 1 wherein the spacer comprises an elastically extensible outer cover.

9. A disposable diaper comprising:
   a liquid impervious backsheet;
   a liquid previous topsheet joined to the backsheet;
   an absorbent core intermediate the backsheet and the topsheet; and
   a spacer joined to the disposable diaper for maintaining a Z direction fecal void space under compressive loading, the spacer comprising:
   a flexible outer cover; and
   a plurality of discrete elements enclosed in the outer cover, each discrete element relatively movable with respect to other discrete elements within the outer cover.

10. A disposable diaper comprising:
    a liquid impervious backsheet;
    a liquid previous topsheet joined to the backsheet to form a fecal void space intermediate the topsheet and the backsheet for receiving fecal matter, the topsheet having an aperture therethrough for communicating fecal matter to the void space;
    an absorbent core intermediate the backsheet and the topsheet; and
    a spacer for maintaining the fecal void space under compressive loading, the spacer joined to the disposable diaper intermediate the topsheet and the backsheet, the spacer comprising:
a flexible outer cover; and
a plurality of discrete elements enclosed in the outer cover, each discrete element relatively movable with respect to other discrete elements within the outer cover.

11. A disposable diaper comprising:
a front waist margin;
a rear waist margin;
a liquid impervious backsheet;
a liquid previous topsheet joined to the backsheet to form a fecal void space for receiving fecal matter, intermediate the topsheet and the backsheet the topsheet having an aperture therethrough for communicating fecal matter into the void space;
an absorbent core intermediate the backsheet and the topsheet; and
a spacer for maintaining the fecal void space under compressive loading, the spacer joined to the disposable diaper intermediate the topsheet and the backsheet, the spacer registered with the aperture in the topsheet and comprising:
a flexible outer cover; and
a plurality of discrete elements enclosed in the outer cover, each discrete element relatively movable with respect to other discrete elements within the outer cover.

12. The disposable diaper recited in claim 11 wherein the spacer comprises a generally closed figure having an opening registered with the aperture in the topsheet.

13. The disposable diaper recited in claim 11, wherein the discrete elements have a generally rounded surface.

14. The disposable diaper recited in claim 13 wherein the discrete elements have a generally spherical shape.

15. The disposable diaper recited in claim 14 wherein the plurality of discrete elements comprise generally spherical expanded polystyrene beads.

16. The disposable diaper recited in claim 11 wherein the spacer is positioned between the topsheet and the absorbent core.

17. The disposable diaper recited in claim 11 wherein the absorbent core comprises an upper layer and a lower layer, and wherein the spacer is positioned between the upper and lower layers of the absorbent core.

18. The disposable diaper recited in claim 11 wherein the spacer has a packing density of less than 60 percent.

19. The disposable diaper recited in claim 18 wherein the spacer has a packing density of between 20 and 50 percent.

20. The disposable diaper recited in claim 19 wherein the spacer has a packing density of between 20 and 30 percent.

21. The disposable diaper recited in claim 11 wherein the spacer comprises a plurality of separate compartments.

22. The disposable diaper recited in claim 21 wherein at least one of the separate compartments has a substantially different packing density than another of the separate compartments.

23. The disposable diaper recited in claim 22 wherein the spacer has a first compartment with a first relatively high packing density, and a second compartment with a second relatively low packing density, wherein at least a portion of the second compartment is positioned intermediate the aperture through the topsheet and the front waist margin.

24. The disposable diaper recited in claim 11 wherein the spacer comprises an elastically extensible outer cover.

25. The disposable diaper recited in claim 11 wherein the spacer maintains a Z-direction thickness of at least 0.64 centimeters under a compressive Z-direction load of at least 350 kilograms per square meter having a circular footprint of no more than 6.45 square centimeters.

* * * * *

UNITED STATES PATENT AND TRADEMARK OFFICE
CERTIFICATE OF CORRECTION

PATENT NO. : 5,306,266
DATED : APRIL 26, 1994
INVENTOR(S) : M. ELAINE FREELAND

It is certified that error appears in the above-identified patent and that said Letters Patent is hereby corrected as shown below:

On the title page, item [56]:

| | |
|---|---|
| Under References Cited U.S. PATENT DOCUMENTS | delete "7,811,206 12/1993" and insert therefor --7,811,206 12/1991--. |
| Column 5, line 6 | delete "and, incorporate" and insert therefor --and incorporate--(delete the comma). |
| Column 16, line 23 | delete "discreate" and insert therefor --discrete--. |
| Column 16, line 60 | delete "previous" and insert therefor --pervious--. |
| Column 17, line 12 | delete "previous" and insert therefor --pervious--. |

Signed and Sealed this

Thirteenth Day of December, 1994

*Attest:*

BRUCE LEHMAN

*Attesting Officer*     *Commissioner of Patents and Trademarks*